United States Patent [19]
Kesling

[11] Patent Number: 6,135,767
[45] Date of Patent: Oct. 24, 2000

[54] SPRING LOOP RETAINER AND METHOD OF MAKING SAME

[75] Inventor: Christopher K. Kesling, LaPorte, Ind.

[73] Assignee: TP Orthodontics, Inc., Westville, Ind.

[21] Appl. No.: 09/356,664

[22] Filed: Jul. 19, 1999

[51] Int. Cl.[7] ........................ A61C 3/00
[52] U.S. Cl. ........................ 433/21
[58] Field of Search ............... 433/18, 20, 21, 433/22

[56] References Cited

U.S. PATENT DOCUMENTS

| | | | |
|---|---|---|---|
| 1,361,661 | 12/1920 | Alexander | 433/20 |
| 3,994,068 | 11/1976 | Goshgarian . | |
| 4,299,568 | 11/1981 | Crowley . | |
| 4,676,745 | 6/1987 | Zurita | 433/18 |
| 4,849,032 | 7/1989 | Kawaguchi | 433/21 |
| 5,022,855 | 6/1991 | Jeckel | 433/18 |
| 5,167,499 | 12/1992 | Arndt et al. | 433/18 |
| 5,312,247 | 5/1994 | Sachdeva et al. | 433/18 |
| 5,683,245 | 11/1997 | Sachdeva et al. | 433/20 |

OTHER PUBLICATIONS

"Spring Aligners", TP Orthodontics, Inc. Catalog, pp. 185–186 (1992).

*Primary Examiner*—Todd E. Manahan
*Attorney, Agent, or Firm*—Lloyd L. Zickert

[57] ABSTRACT

An orthodontic appliance for correcting minor incisor irregularities and/or retaining incisors in orthodontically corrected positions, which includes a labial plate engaging the labial surfaces of the incisors, a lingual bar or plate engaging the lingual incisal surfaces, and shape memory wire interconnecting the ends of the labial plate with the lingual bar and resiliently urging the plate and bar toward each other so that when the appliance is mounted on the teeth of a patient, it will actively and continuously grip the incisors for tooth control and to prevent dislodgement.

24 Claims, 2 Drawing Sheets

SPRING LOOP RETAINER AND METHOD OF MAKING SAME

DESCRIPTION

This invention relates in general to an orthodontic appliance for correcting minor incisor irregularities and/or retaining the position of orthodontically corrected teeth, and more particularly to a preformed continuously activated orthodontic retainer for the incisors which includes a labial means or plate and a lingual means or bar contacting some or all of the incisors that are resiliently urged together in order to continuously grip the teeth when in place on the incisors.

BACKGROUND OF THE INVENTION

Heretofore, it has been known to provide various types of appliances for correcting minor incisor irregularities and for retaining teeth in corrected position for either the lower or upper anterior teeth. One such appliance is made and sold by TP Orthodontics of LaPorte, Ind., under the trademark "Spring Aligner." Such an appliance includes an acrylic labial plate and a lingual acrylic bar connected by stainless steel wire to fit over the incisors of a patient. The appliance is custom-made by making it over a plaster model of a patient's teeth, or by making it over a set-up. An inherent problem of this appliance is that it becomes loose after worn several weeks and requires repeated re-tightening and reactivation to be effective to maintain the alignment of the incisors.

SUMMARY OF THE INVENTION

The present invention overcomes this problem of the heretofore known appliances by including biasing means for continually urging the labial and lingual portions of the appliance toward each other thereby producing a gripping action of the teeth during all times when it is worn by a patient. This gripping action overcomes the problem of requiring re-tightening as the heretofore known "Spring Aligner" appliance of the prior art demanded.

It is therefore, an object of the present invention to provide a new and improved orthodontic appliance for correcting minor incisor irregularies and maintaining the teeth in an ideal position that does not require re-activation.

A further object of the present invention is in the provision of an orthodontic appliance for use in correcting minor incisor irregularities and for retaining the corrected positions of the teeth wherein the appliance includes means for causing the appliance to always grip the teeth when it is worn, even when the teeth have reached their ideal positions.

A still further object of the present invention is to provide a new and improved orthodontic appliance for correcting minor incisor irregularities and/or retaining the corrected positions of the teeth in ideal positions, and which includes resilient wire loops connected between opposite ends of a labial plate and a lingual bar which remains continuously activated to cause a continuous gripping of the teeth and move the teeth to their ideal positions and thereafter retain those positions.

Other objects, features, and advantages of the invention will be apparent from the following detailed disclosure, taken in conjunction with accompanying sheet of drawings, wherein like reference numerals refer to like parts.

DETAILED DESCRIPTION OF THE INVENTION

Figure 1:
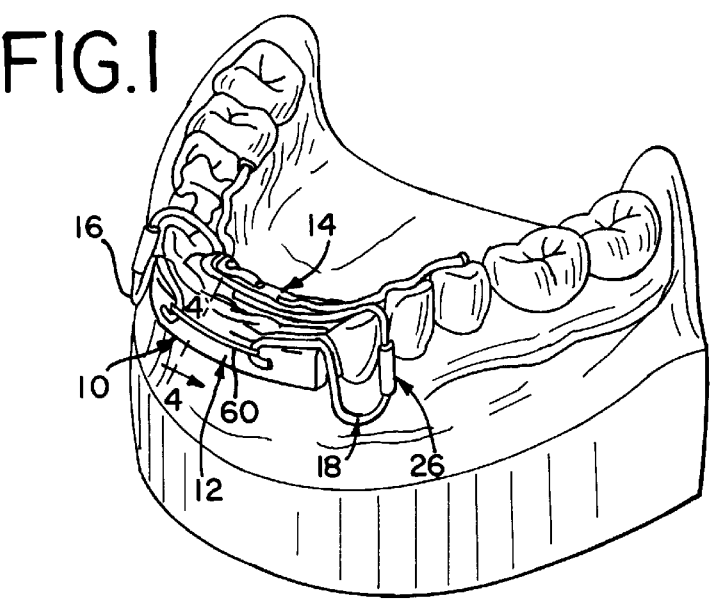
FIG. 1 is a perspective view of a plaster model or a set-up on which an appliance according to the present invention is mounted, wherein the model of the teeth is for a lower arch.
Figure 4:
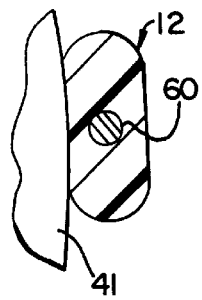
FIG. 4 is an enlarged detailed sectional view taken substantially along line 4—4 of FIG.
Figure 2:
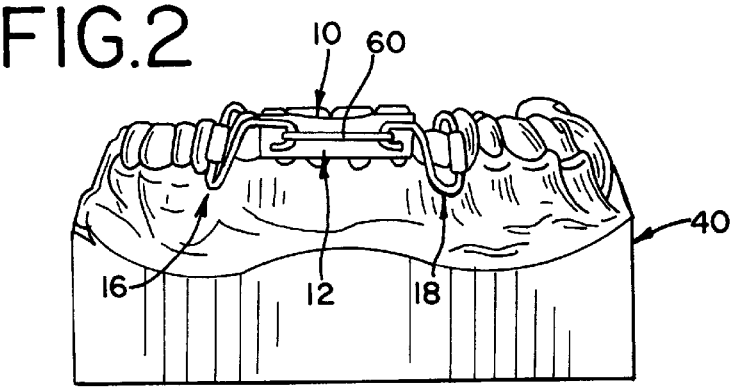
FIG. 2 is a front elevational view of the plaster model and appliance shown in FIG. 1.
Figure 3:
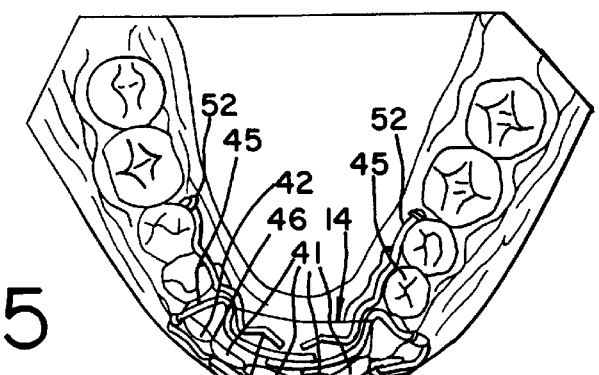
FIG. 3 is a top-plan view of the plaster model and appliance shown in FIG. 1.

Referring now to the drawings and particularly to FIGS. 1 to 3, the preferred embodiment of the present invention is shown, wherein it comprises an orthodontic retaining appliance generally indicated by the numeral 10. The appliance 10 is shown in mounted position on a plaster model of teeth in FIGS. 1–3. It will be appreciated that the appliance will be custom-made for a patient over a plaster model or a set-up of the patient's teeth. The set-up may only need to be a partial set-up of the incisors over which the appliance of the present invention may be made, or it may be a full set-up. In either case, it is well-known that a set-up constitutes rearranging teeth to their ideal positions. It will also be appreciated that the appliance will generally be made to bring some or all of the incisor teeth into ideal positions so that it can correct minor incisor irregularities and then thereafter retain those teeth in the corrected positions until they are firmly set.

The appliance of the invention eliminates the problem of loss of activation over time which heretofore required periodic re-activation.

The retainer of the invention, as shown in FIGS. 1 to 4, generally includes a labial plate 12 and a lingual bar or strap 14. The plate and bar are resiliently urged toward one another by shape memory spring loops 16 and 18 connected between the plate and the bar. It will be appreciated that both the plate and the bar are formed to conform to the outer contours of the teeth. Thus, the teeth engaging sides will have teeth impressions to mate closely with the teeth when in ideal positions. The continual urging together of the labial plate and lingual bar enables the retainer to be continuously grippingly held in place on the incisors even after the teeth have reached their ideal positions.

The orthodontic retainer, illustrated in FIGS. 1–3, is shown on a plaster model or setup in position on the incisors of a lower arch. It can be appreciated that the orthodontic retainer of the present invention is a preformed appliance and custom-made for a patient although it should also be appreciated that such retainers could be made in various sizes to be immediately used during orthodontic treatment following the removal of fixed appliances. Moreover, the retainer could be made over a partial set-up of either the upper or lower anterior teeth, or could be made over a full set-up of the teeth, or over a model on which none of the teeth have been moved.

The labial or lingual plates or bars are preferably made of a clear polymer, such as a castable acrylic. However, the polymer may be colored or opaque, if desired. A suitable acrylic could be the cold cure orthodontic acrylic marketed by TP Orthodontics under the mark ORTHO CRYLIC. It should also be appreciated the plates or bars could be made of cast metal.

Figure 5:
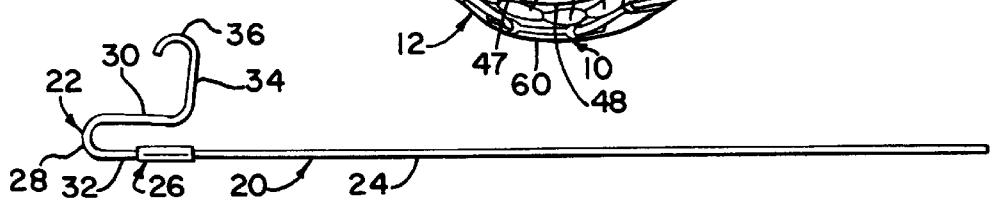
FIG. 5 is an elevational view of a spring loop component used in making the orthodontic appliance that is shown in FIGS. 1 to 3.

The appliance of the invention is preferably made from a pair of activation loop components 20 of the type shown in FIG. 5, which would include a spring loop 22 of shape memory wire connected to a straight length of ordinary 18-8 stainless steel wire 24 by means of a connecter 26, as seen in FIG. 5. Any suitable connecting means may be used to connect the loop 22 to the anchoring wire 24. Preferably, the connector will be in the form of a single tube or sleeve sized to closely receive the ends of the wires 22 and 24. The tube would be crimped at each wire and then soldered to the wires. The wire spring loop 22 is shown in a non-activated state and includes a U-shaped form having a bite portion 28 merging with spaced apart legs or arms 30 and 32. The leg 32 fits into one end of the tube connecter 26 and the anchoring wire 24 fits into the other end of the connector. The leg 30 of the spring loop 22 has extending from its free end a straight portion 34 which terminates in a hook-shaped portion 36 that is intended to be embedded in the labial plate 12 and also serve for interconnection by use of a suitable filament or ligature wire 60 to a like hook-shaped end of a spring loop at the other end of the plate. After completion of the appliance and the curing of the acrylic bars, it may be removed from the plaster model or setup and thereafter be placed in the patient's mouth.

Thus, the preferred embodiment of the invention would include the use of a pair of spring loop components 20 that are positioned and formed on a plaster model or set-up so that they can be connected between the labial plate and the lingual bar to form the retaining appliance of the invention. The plaster model or set-up shown in FIGS. 1 to 3 includes the four incisors 41, adjacent canines 42, and bicuspids and molars.

With respect to the spring loop component 20, the straight wire 24 would be of a suitable stainless steel as would the tube connecter 26, while the spring loop 22 could be of a suitable shape memory wire. One satisfactory shape memory wire would be Reflex nickel titanium wire marketed by TP Orthodontics, which owns the trademark REFLEX. In any event, the spring loop would be in an inactive state when provided in the spring loop component, as shown in FIG. 5, and thereafter, when mounted to form the retainer, would be activated such that the opposed legs or arms 30 or 32 would be somewhat separated from each other so that they could apply force to the lingual bar and labial plate and move the teeth to their desired positions. When the spring loops are made of an appropriate heat-activated wire, the spring loops would be dead soft at room temperature and activated by the temperature in the mouth when worn by a patient, at which time the spring loops would function to urge the labial plate and lingual bar toward one another.

As seen in FIGS. 1 to 3, the U-shaped spring loops, 16 and 18, are disposed along the labial at opposite ends of the labial plate 12. Likewise, the tubular connecters between the spring loops 22 and anchoring wires 24 will be disposed along the labial and adjacent the canines. The anchoring wire 24 of each spring loop, will be embedded in the lingual bar 14 while the shaped ends of the spring loops will be embedded in the labial plate 12.

The retaining appliance of the present invention can be custom made over a set-up or a plaster model by first disposing a spring loop component, as shown in FIG. 5, at each of the canines and bending over the straight wire 24 at bends 45 so that it extends over the canines adjacent to their distal ends. Then a small loop 46 is formed along the lingual of the teeth so that the anchoring wire extends along the lingual of the incisors, and the end of the anchor wire is appropriately cut from each spring loop appliance so that the ends 47 and 48 are preferably in slightly overlapping relationship along the lingual of the incisors. The labial acrylic plate is then formed embedding these ends, as shown in FIG. 3, for anchoring the spring loop in place on the lingual bar 14. Additionally, if desired, stabilizing wires 52 may be suitably formed to lay along the lingual of the canine and the bicuspids, as well as being anchored in the lingual bar to provide additional stability to the overall appliance.

The other ends of the spring loops are then anchored in the labial plate 12 which is formed along the labial of the incisors, wherein the hooked ends 36 are embedded in the labial plate. A filament is provided for interconnection between the hooks of the opposed spring loops to hold them in place. The filament may be in the form of a monofilament thread or a steel ligature tie as designated by the numeral 60 in FIG. 2. When placing the filament 60 and connecting it to the hooked ends of the spring loops the spring loops are activated so that once anchored in the labial plate, the spring loops will then cause the plate and lingual bar to be urged resiliently toward one another.

In a modification of the invention, the spring loops could be formed at the opposite ends of a single length of shape memory wire which would eliminate the need for a connecting filament.

Figure 6:
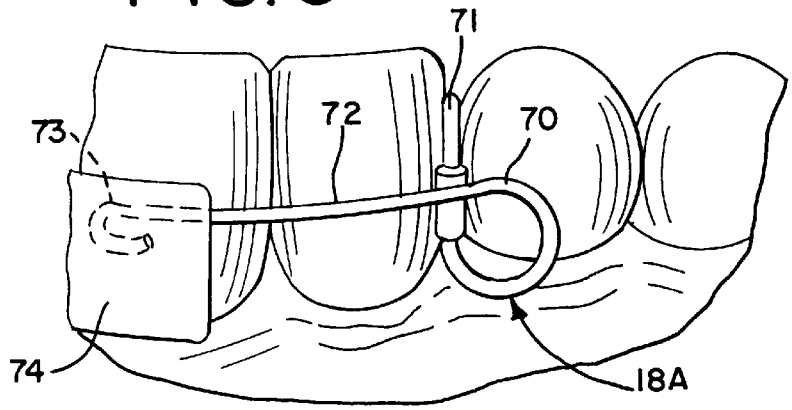
FIG. 6 is an enlarged elevational view of a modified spring loop in accordance with the invention.

A modified spring loop 18A is shown in FIG. 6 which differs from the spring loop 18 in the embodiment of FIGS. 1 to 3 in that the loop is generally closed and coil shaped as viewed labially. The loop 18A is connected at one end by a connector 70 to an anchoring wire 71 which is received by the lingual bar that is not shown but would be like the bar 14 in embodiment of FIGS. 1 to 3. The other end of the loop is integral with a straight section 72 that terminates in a bent-over end 73 embedded in the labial plate 74 at the labial of the incisors. This spring loop configuration functions like the loop 18 to apply forces to the labial plate and the lingual bar and grip the incisors.

Figure 7:
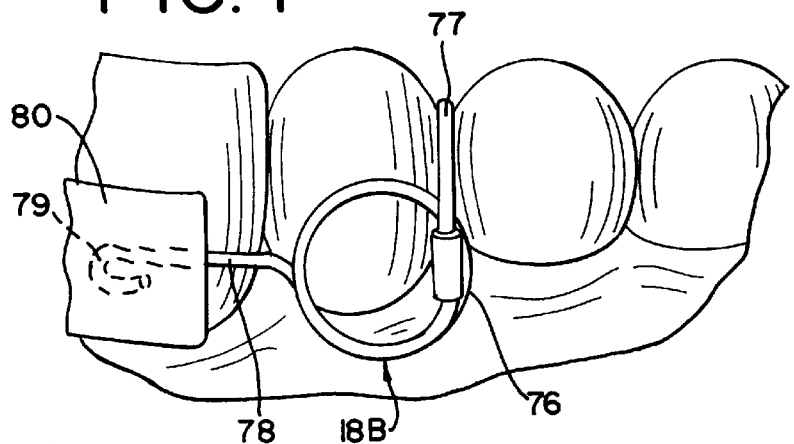
FIG. 7 is a view like FIG. 6 showing a still further modified spring loop in accordance with the present invention.

A further modified spring loop 18B is shown in FIG. 7 to illustrate that the spring loop may take any number of forms.

This spring loop includes a complete coil wherein one end is received by the connector 76 that is in turn connected to the anchoring wire 77 which will be received by the lingual bar of the appliance. The other end of the coil spring loop is connected to a straight section 78 which terminates in a bent-over end 79 received in the labial plate 80. This spring loop will function much the same as the spring loop 18 of the embodiment of FIGS. 1 to 3 in that it will serve to apply forces to the lingual bar and the labial plate to grippingly engage the incisors. The extra portion of the coil of this spring loop would provide an additional force component over the spring loops in the embodiment of FIGS. 1 to 3 and the embodiment of FIG. 6. It will be appreciated that the spring loops 18a and 18b of the embodiments of FIGS. 6 and 7 will likewise be made of a shape memory wire.

Figure 8:
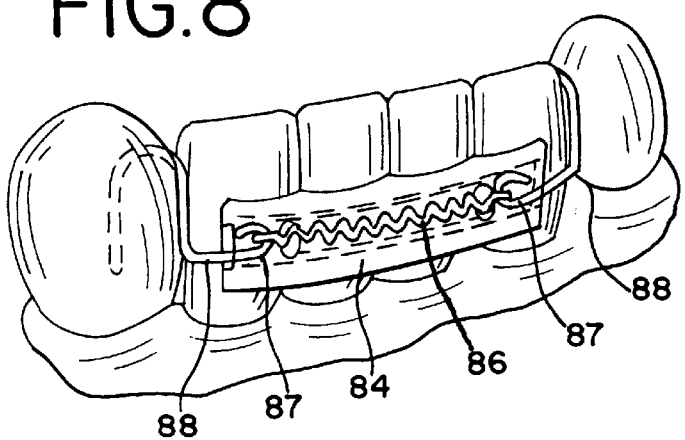
FIG. 8 is a front elevational view of a further modification of the present invention showing a shape memory coil spring received in a labial plate.
Figure 9:
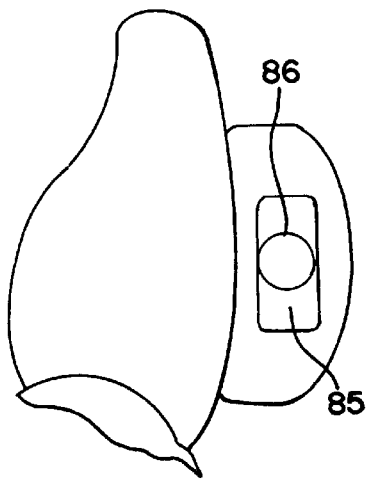
FIG. 9 is an enlarged end elevational view of the labial plate in FIG. 8.

Another embodiment of the invention is shown in FIG. 8 which differs in that the shape memory wire is in the form of a coil spring received in the labial plate. In this embodiment the labial plate 84 is provided with a longitudinally extending through hole 85 that is rectangular in cross section and in which extends a shape memory coil spring 86 connected under stress to opposite hook-shaped ends 87 of anchoring wires 88. The anchoring wires would be of stainless steel and would extend over the arch and be suitably anchored in a lingual bar such as shown in the embodiment of FIGS. 1 to 3. It will be appreciated that the labial plate 84 will have teeth impressions to fit against the labial side of the incisors and be made of a suitable material such as acrylic. Rotational control of the labial plate is obtained by the connecting hooks 87 on the stainless steel anchoring wires 88 which are received within the rectangular opening 85. The hook-shaped ends extend along a plane substantially parallel with the labial faces of the incisors and therefore are connected to the labial plate against rotation of the plate and the wires. Thus, the hook-shaped ends 87 will be received within the rectangular opening 85. The shape memory coil spring 86 may be replaced with one of more or less spring force to increase or decrease the forces between the labial plate and the lingual bar. It will be appreciated that this embodiment will function much in the same manner as the embodiment in FIGS. 1 to 3 in the application of a gripping force of the appliance to the incisors.

It will be understood that modifications and variations may be affected without departing from the scope of the novel concepts of the present invention, but it is understood that this present application is to be limited only by the scope of the appended claims.

What is claimed is:

1. An orthodontic retainer for correcting minor incisor irregularities of a patient and/or retaining the corrected teeth positions, said retainer comprising:

means engaging the labial and lingual surfaces of at least two anterior teeth, and means connected to said labial and lingual engaging means for continuously urging the labial and lingual engaging means to move toward each other and grip the incisors and retain the retainer in place on the teeth, said urging means including a material having a shape memory characteristic.

2. The retainer of claim 1, wherein said urging means includes at least one spring loop of shape memory wire.

3. The retainer of claim 2, wherein said shape memory wire is formed of a material which is activated by the heat in the mouth when the appliance is worn.

4. The retainer of claim 2, wherein each loop includes an end connected to the labial engaging means, and an end connected to the lingual engaging means.

5. The retainer of claim 2, wherein when the labial means engages the labial surfaces of the incisors and the lingual means engages the lingual surfaces of the incisors, and each loop is disposed along the labial of the teeth and includes a first end embedded in the labial means, means connecting said labially embedded ends prior to forming the labial means, and a second end connected to an anchoring wire embedded in the lingual means.

6. The retainer of claim 5, wherein a tube interconnects each second end of the loop to a respective anchoring wire.

7. The retainer of claim 6, wherein the tube is crimped and soldered to the loop and anchoring wires.

8. The activatable loop component of claim 7, wherein said connecting means is a tubular member that receives an end of the loop and an end of the wire anchor.

9. The retainer of claim 1, wherein said urging means includes a pair of spring loops of shape memory wire.

10. The retainer of claim 1, wherein said labial means and lingual means are acrylic.

11. The retainer of claim 1, wherein said labial means and lingual means are cast metal.

12. The retainer of claim 1, wherein said labial and lingual engaging means include teeth impressions for mating with the respective teeth surfaces.

13. A method of making an orthodontic retainer for correcting minor incisor irregularities of a patient and/or retaining the corrected teeth positions, wherein the retainer is made from acrylic and a pair of activation loop components, each of said components including a shape memory loop having spaced ends and an anchoring wire connected to one of said ends, said method comprising the steps of: making the retainer over a standard plaster model or a set-up, forming an acrylic lingual bar and embedding the anchoring wire of each component in the lingual bar, activating the loops, connecting the loops in activated positions, and forming a labial acrylic plate and embedding the other ends of said loops in said labial plate.

14. An activatable loop component for use in a retainer for correcting minor incisor irregularities and/or retaining the incisors in corrected positions wherein the retainer includes a labial plate and a lingual bar, said component comprising: a U-shaped loop of shape memory wire having an anchoring portion on one end for connection to the labial plate, and a wire anchor connected to the other end by a connecting means, wherein the wire anchor is connectable to the lingual bar.

15. The method of claim 14, which further comprises the step of connecting the loops together across the labial surfaces of the incisors to hold them in activated/open positions prior to forming the labial acrylic plate.

16. The method of making an activatable loop component for use in a retainer for correcting minor incisor irregularities and/or retaining the incisors in corrected position, wherein the retainer includes an acrylic labial plate and an acrylic lingual bar to be resiliently urged toward each other by a pair of said components, and said method comprises the steps of: providing a U-shaped loop of resilient shape memory wire having spaced ends, one end of which is connected to the acrylic plate, connecting a length of anchoring wire to the lingual bar, and connecting the other end of the shape memory wire to the anchoring wire.

17. An activatable component for use in a retainer for correcting minor incisor irregularities and/or retaining the incisors in corrected positions wherein the retainer includes a labial plate and a lingual bar, said component comprising a length of shape memory wire having a pair of spaced-apart U-shaped loops, a pair of anchor wires, and means connectable to the anchor wires to the loops.

18. An orthodontic retainer for correcting minor incisor irregularities of a patient and/or retaining the corrected teeth positions, said retainer comprising:

shape memory wire for continuously applying forces to the labial and lingual surfaces of at least two anterior teeth to enhance retention of said retainer.

19. The retainer of claim 18, wherein said shape memory means includes at least one loop member of shape memory wire.

20. The retainer of claim 18, wherein said shape memory means includes a plurality of loop members of shape memory wire.

21. The retainer of claim 18, wherein said shape memory means includes a pair of loop members of shape memory wire.

22. The retainer of claim 18, wherein said shape memory means includes a coil of shape memory wire.

23. The retainer of claim 22, wherein said coil of wire engages the labial surface of said anterior teeth.

24. An orthodontic retainer for correcting minor incisor irregularities of a patient and/or retaining the corrected teeth positions, said retainer comprising:

a labial plate of acrylic for engaging the labial surfaces of at least two anterior teeth, a lingual bar of acrylic for engaging the lingual surfaces of at least two anterior teeth, an opening extending mesiodistally through said labial plate, a coil spring of shape memory wire in said opening, and wire connecting means at each end of said coil spring connected to said lingual bar.

* * * * *